United States Patent [19]

Ogasawara et al.

[11] Patent Number: 5,015,631
[45] Date of Patent: May 14, 1991

[54] REPAIRING AGENT FOR CELLS AND TISSUES

[75] Inventors: Sadanori Ogasawara, Tokorozawa; Kenji Abiko, Kaminoyama; Masayoshi Ito, Kunitachi; Yoshiyasu Shitori, Tokyo, all of Japan

[73] Assignee: MECT Corporation, Japan

[21] Appl. No.: 211,226

[22] Filed: Jun. 24, 1988

[30] Foreign Application Priority Data

Jun. 25, 1987 [JP] Japan ................. 62-158707

[51] Int. Cl.$^5$ .................. A61K 31/00; A61F 13/00
[52] U.S. Cl. .................. 514/53; 514/23; 514/888; 424/434; 536/17.9; 536/121
[58] Field of Search ............ 514/53, 23, 888; 424/434; 536/17.9, 121

[56] References Cited

U.S. PATENT DOCUMENTS

| | | | |
|---|---|---|---|
| 4,447,600 | 5/1984 | Ogura et al. | 536/23 |
| 4,675,391 | 6/1987 | Shibayama et al. | 536/17.4 |
| 4,698,332 | 10/1987 | Ogasawara et al. | 514/42 |
| 4,713,374 | 12/1987 | Della Valle et al. | 514/54 |

FOREIGN PATENT DOCUMENTS

| | | | |
|---|---|---|---|
| 177783 | 4/1986 | European Pat. Off. | |
| 230322 | 7/1987 | European Pat. Off. | 536/122 |
| 61-289037 | 12/1986 | Japan | |
| 62-223123 | 10/1987 | Japan | |
| 48707 | 1/1986 | United Kingdom | 536/122 |

Primary Examiner—Ronald W. Griffin
Assistant Examiner—Everett White
Attorney, Agent, or Firm—Jacobs & Jacobs

[57] ABSTRACT

A repairing agent for cells and tissues is disclosed, which agent comprises, as an active ingredient, a compound of the general formula:

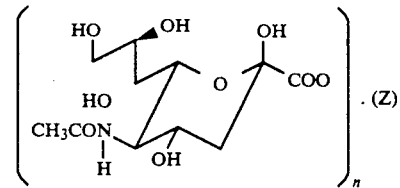

wherein Z represents lithium, potassium, sodium, ammonium or an organic ammonium when n is 1, and Z represents calcium, barium or magnesium when n is 2.

2 Claims, No Drawings

REPAIRING AGENT FOR CELLS AND TISSUES

FIELD OF THE INVENTION

The present invention relates to a repairing agent for cells and tissues. In particular, the present invention relates to a repairing agent for cells and tissues of living bodies, particularly a repairing agent comprising an N-acetylneuraminic acid salt and effective for relieving nasal obstruction symptoms of a mucous membrane.

PRIOR ART

Otorhinologic diseases include rhinitis and allergic rhinitis. The rhinitis is caused by a climatic change or a cold and induced by chemical or mechanical stimulation. The symptoms of the rhinitis include rhinorrhea, nasal obstruction, obstruent rhinolalia, etc.

The allergic rhinitis belongs to I-type allergy. It is a nasal disease resulting form an allergic reaction in the nasal mucous membrane. Its symptoms include paroxysmal or recurrent sneezes, sniffles, and nasal obstruction. These symptoms are brought about by disappearance of cilia of nasal mucous membrane, degeneration of the epithelium, etc.

The mechanism of the action of a remedy for the rhinitis and allergic rhinitis used heretofore was as follows: it stimulates the α-receptor and the sympathetic nerves to contract the peripheral blood vessels, thereby healing hyperemia and swelling of the nasal mucous membrane.

However, the conventional remedies have problems such as that it might induce a blood pressure elevation and that their effective time is short. Further, although adrenocortical steroids are used as anti-inflammatory drugs, the hormonal safety has become an issue.

Recently developed remedies for the allergic rhinitis have an effect of inhibiting the liberation of chemical mediators from mast cells when the I-type allergic reaction occurs and also have an antagonistic effect.

The mechanism of the present repairing agent for repairing cells and tissues is utterly different from the above-described mechanisms. The former is capable of remarkably relieving the nasal obstruction symptoms which are considered to be the most unpleasant ones among the rhinitis symptoms.

Further, the present repairing agent is usable as eye drops for the treatment of diseases caused by a degeneration of mucous membranes of eyes, or as a cosmetic for maintaining the elasticity of skin.

Investigations have been made on the pharmacological effects of N-acetylneuramini acid. It was reported that this compound has antiviral and anti-inflammatory effects [see Robert L. Hirsch et al., "The Journal of Immunology", 127, No. 5, p.1740 to 1743 (1981); P. Görög et al., "Agent and Actions", 8, No. 5, p.543 to 545 (1978); and Hiromi Ito et al., "Yakuri to chiryo (Pharmacology and Treatment)", 13, No. 7, p.479 to 494 (1985)].

A salt of N-acetylneuraminic acid can be prepared by neutralizing N-acetylneuraminic acid with a hydroxide or carbonate of an alkali metal or alkaline earth metal and then separating the alkali metal salt or alkaline earth metal salt from the reaction system [see Japanese Patent Unexamined Published Application (hereinafter referred to as "J.P. KOKAI") No. 62-223123 ].

The inventors previously developed expectorants containing an N-acetylneuraminic acid salt as an effective ingredient (see J.P. Kokai Nos. 61-289037 and 61-68418).

The present inventors have found that N-acetylneuraminic acid salts can repair cells and tissues in nasal mucous membranes. After intensive investigations, the present inventors have found that these salts relieve the nasal obstruction symptoms The present invention has been completed on the basis of this finding.

SUMMARY OF THE INVENTION

An object of the present invention is to provide a repairing agent for cells and tissues capable of remarkably relieving nasal obstruction symptoms which are usually the most unpleasant ones among the rhinitis symptoms by using a mechanism utterly different from that of conventional repairing agents.

The present invention relates to a repairing agent for cells and tissues which contains, as an effective ingredient, a compound of the general formula:

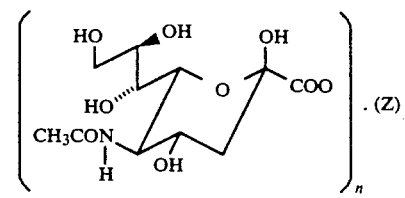

wherein Z represents lithium, potassium, sodium, ammonium or an organic ammonium when n is 1, and Z represents calcium, barium or magnesium when b is 2.

The compound of the present invention is locally applied. Namely, it is used in the form of fine particles as a nostril spray or in the form of a solution as nostril drops. Or a disc containing it is applied to the mucous membrane of the nostril.

The following Examples and Reference Examples will further illustrate the effective and formulations of the present repairing agent.

EXAMPLE 1

The effects of test samples on acute disappearance of cilia from nasal mucous membranes of rats and the degeneration of the epithelium induced by exposure to sulfur dioxide:

(1) Experimental animals

Male Wistar rats weighing 180 to 200 g were used.

(2) Material

Sodium N-acetylneuraminate (a product of MECT Corporation) was used.

(3) Experimental method

The rats were exposed to 400 ppm of sulfur dioxide for 4 hours. 30 minutes after the exposure, the rats were caused to inhale the test sample or physiological saline as follows:

Group I: inhalation of 300 mg/m³ of sodium N-acetylneuraminate for 1 hour.

Group II: inhalation of 100 mg/m³ of sodium N-acetylneuraminate for 1 hour.

Group III: inhalation of 20 ml/m³ of the physiological saline for 1 hour.

Each group comprised 5 rats.

24 hours after the inhalation of the materials or physiological saline, the rats were killed and their intranarial changes were examined by a microscopic observation and the results were compared with one another.

(4) Results

As shown in Table 1, the disappearance of cilia, the monolayer squamous metaplasia of epithelium, and the disappearance of the epithelium were observed as intranarial changes.

These changes were remarkable particularly in Group III. In Groups I and II, only the disappearance of cilia was observed and the degree of the disappearance was lower than that of Group III.

(5) Judgement

The results suggest that sodium N-acetylneuraminate has a remarkable effect of inhibiting the acute disappearance of cilia, monolayer squamous metaplasia and also disappearance of epithelium in the nasal mucous membranes of the rats induced by the exposure to sulfur dioxide.

TABLE 1

| | Histopathological findings of nasal cavity | | |
|---|---|---|---|
| | Disappearance of cilia | Monolayer squamous metaplasia of epithelium | Disappearance of epithelium |
| Group I | | | |
| I-1 | + + | — | — |
| I-2 | + | — | — |
| I-3 | + + | — | — |
| I-4 | + | — | — |
| I-5 | + | — | — |
| Group II | | | |
| II-1 | + | — | — |
| II-2 | — | — | — |
| II-3 | + | — | — |
| II-4 | + + | — | — |
| II-5 | + | — | — |
| Group III | | | |
| III-1 | + + + | + + + | — |
| III-2 | + + | + + + | + + |
| III-3 | + + + | + + + | + |
| III-4 | + + | — | — |

Grade: —: Unchanged + +: Moderate change
Grade: +: Slight + + +: Severe

It is apparent from the results shown in Table 1 that the N-acetylneuraminic acid salt has a remarkable effect of inhibiting the degeneration of the cells and tissue of the nasal mucous membranes and, therefore, it is expected as a repairing agent for the cells and tissues.

EXAMPLE 2

Effects on subacute disappearance of cilia from nasal mucous membrane of rabbits and degeneration of the epithelium thereof induced by exposure to sulfur dioxide:

(1) Experimental animals

Male New Zealand White rabbits weighing 1.8 to 2.2 kg were used.

(2) Test sample

Sodium N-acetylneuraminate (a product of MECT Corporation) was used.

Experimental method

The rabbits were exposed to sulfur dioxide by means of a sulfur dioxide-exposing apparatus for 2 hours a day continuously for 5 weeks. The sulfur dioxide concentrations were 70 to 150 ppm in the first and second weeks and 200 to 300 ppm in the third to fifth weeks. After the third week, the inhalation of the material or physiological saline by means of an ultrasonic nebulizer (TUR-3200: a product of Nippon Koden Co., Ltd.) was made immediately before the exposure to sulfur dioxide.

Group I: inhalation of 25 mg/kg of sodium N-acetylneuraminate for 2 minutes.

Group II: inhalation of 1 ml of physiological saline for 2 minutes.

Each group comprised six rabbits.

Five weeks after completion of the exposure to sulfur dioxide, the rabbits were killed by venesection and the intranarial changes of them were examined by a microscopic observation and the results were compared with one another.

(4) Results

As shown in Table 2, the disapperance of cilia and the squamous metaplasia of epithelium were observed in Groups I and II. The squamous metaplasia of epithelium was more serious in Group II than in Group I.

(5) Judgement

The results suggest that sodium N-acetylneuraminate has a remarkable effect of inhibiting the subacute disappearance of cilia and squamous metaplasia of epithelium in the nasal mucous membrane of rabbits induced by the exposure to sulfur dioxide, and therefore that is has the effect of repairing the cells and tissues.

TABLE 2

| | Histopathological findings of nasal cavity | |
|---|---|---|
| | Disappearance of cilia | Squamous metaplasia of epithelium |
| Group I | | |
| I-1 | — | — |
| I-2 | + | + |
| I-3 | + | + |
| I-4 | + + | + + |
| I-5 | + | + |
| I-6 | + | + |
| Group II | | |
| II-1 | + + + | + + + |
| II-2 | + + + | + + + |
| II-3 | + + + | + + + |
| II-4 | + + + | + + + |
| II-5 | + + + | + + |
| II-6 | + + + | + + + |

Grade: —: Unchanged + +: Moderate change
Grade: +: Slight + + +: Severe

It is apparent from the results shown in Table 2 that the N-acetylneuraminate has a strong effect of repairing the cells and tissues of the nasal mucous membranes and, therefore, it is expected as a repairing agent for the cells and tissues.

EXAMPLE 3

Acute toxicity test:

The acute toxicity tests of sodium N-acetylneuraminate to mice, rats and guinea pigs given by oral administration or subcutaneous injection, intraperitoneal injection, intravenous injection or inhalation, were conducted as follows:

(1) Experimental animals
  ICR mice (6 weeks old)
  SD rats (6 weeks old)
  Hartley guinea pigs (6 weeks old)
(2) Concentration of the chemical
  20 w/v % (solution in distilled water)
(3) Number of animals of each level
  10
(4) Period of observation
  14 days
(5) Method of calculation of $LD_{50}$
  Probit method.

The results are shown in Table 3.

TABLE 3

| Animals | Sex | Acute toxicity tests of sodium N-acetylneuraminate $LD_{50}$ (mg/kg) Route of administration | | | | |
|---|---|---|---|---|---|---|
| | | Oral | Subcutaneous | Intraperitoneal | Intravenous | Inhalation |
| Mice | Male | >5,000 | >5,000 | >5,000 | >5,000 | — |
| | Female | >5,000 | >5,000 | >5,000 | >5,000 | — |
| Rats | Male | >5,000 | >5,000 | >5,000 | >5,000 | >4,000 mg/m$^3$ |
| | Female | >5,000 | >5,000 | >5,000 | >5,000 | >4,000 mg/m$^3$ |
| Guinea pigs | Male | — | — | — | >5,000 | — |

In the inhalation, the subjects were exposed to a spray of the compound of the present invention for one hour. Numerals in the parentheses are 95% confidence limits.

EXAMPLE 4

Simple acute toxicity test:

Simple acute toxicity tests of the materials were conducted by intraveous injections for the mice as follows:

1. Materials and method (1) Materials

Lithium, potassium, barium and magnesium N-acetylneuraminates (products of MECT Corporation) were used.

(2) Experimental animals

Male ddy mice

Weight of the animal in the initial stage of the test: 17.7 to 21.1 g

Number of mice for each level: 3

(3) Room temperature: 23±1° C., humidity: 55±7%

(4) Route of administration: intravenous injection (5) Method of administration and dose The material was dissolved in the physiological saline. The concentration of the dose solution was adjusted so that 0.2 ml of the dose solution was administered per 20 g of the body weight of the mice. The solution was given to a tail of each mouse by the intravenous injection. The dose was 500, 1000 or 2000 mg/kg.

(6) Observation of general symptoms and death

The general symptoms and death were observed from immediately after the administration to seven days after the administration.

2. Results (1) Death rates

The death rates are shown in Table 4.

With 1000 mg/kg or 2000 mg/kg of magnesium, barium or potassium N-acetylneuraminates, all of the three mice died. With 500 mg/kg of barium N-acetylneuraminate, all of the three mice died but with 500 mg/kg of other compounds, no mouse died.

(2) General symptoms

The died mice had clonic convulsion and urinary incontinence and most of them died immediately after the administration of within one minute thereafter. In some of the survivals, the inhibition of spontaneous movement was observed but they recovered within one hour.

TABLE 4

| Chemical | Dose mg/kg | Number of death with the elapse of time | | | | | | | | | | Final death rate |
|---|---|---|---|---|---|---|---|---|---|---|---|---|
| | | 1 | 3 | 6 | 24 hrs | 2 | 3 | 4 | 5 | 6 | 7 days | |
| Lithium N-acetylneuraminate | 500 | 0 | 0 | 0 | 0 | 0 | 0 | 0 | 0 | 0 | 0 | 0/3 |
| | 1000 | 0 | 0 | 0 | 0 | 0 | 0 | 0 | 0 | 0 | 0 | 0/3 |
| | 2000 | 0 | 0 | 0 | 0 | 0 | 0 | 0 | 0 | 0 | 0 | 0/3 |
| Potassium N-acetylneuraminate | 500 | 0 | 0 | 0 | 0 | 0 | 0 | 0 | 0 | 0 | 0 | 0/3 |
| | 1000 | 3 | 0 | 0 | 0 | 0 | 0 | 0 | 0 | 0 | 0 | 3/3 |
| | 2000 | 3 | 0 | 0 | 0 | 0 | 0 | 0 | 0 | 0 | 0 | 3/3 |
| Barium N-acetylneuraminate | 500 | 3 | 0 | 0 | 0 | 0 | 0 | 0 | 0 | 0 | 0 | 3/3 |
| | 1000 | 3 | 0 | 0 | 0 | 0 | 0 | 0 | 0 | 0 | 0 | 3/3 |
| | 2000 | 3 | 0 | 0 | 0 | 0 | 0 | 0 | 0 | 0 | 0 | 3/3 |
| Magnesium N-acetylneuraminate | 500 | 0 | 0 | 0 | 0 | 0 | 0 | 0 | 0 | 0 | 0 | 0/3 |
| | 1000 | 3 | 0 | 0 | 0 | 0 | 0 | 0 | 0 | 0 | 0 | 3/3 |
| | 2000 | 3 | 0 | 0 | 0 | 0 | 0 | 0 | 0 | 0 | 0 | 3/3 |

Now, the description will be made on the administration mode of the present nasal drops.

Method of administration

The dose is suitably varied depending on the symptoms of the patients. The compound of the present invention is given every 3 to 5 hours each in an amount of 0.1 to 50 mg by spraying 1 to 3 times or in an amount of 2 to 4 drops.

0.02 to 0.5 ml of the solution is applied by each spraying. The amount of each drop is 0.01 to 0.05 ml.

According to the results of the pharmacodynamic tests of drugs and the acute toxicity tests, the number of times of the administration per day is not limited.

Formulation

The suitable concentration of the compound of the present invention in a preparation is 0.5 to 10.0 wt. %. Sodium N-acetylneuraminate is the most stable in the pH range of 5.5 to 6.0. Since the ionic strength scarcely exerts influence on the effect of this compound, any of additives which have been already accepted as the additives for sprays and inhalants (for internal use), may be usable. However, the additives are not limited to them. Examples of the formulations will be given below, which by no means limit the scope of the present invention. Incidentally, variations and modifications of buffering agents and antiseptics and various combinations of an isotonizing agent, stabilizer, thickening agent and base (hereinafter referred to as carriers) can be employed if necessary.

EXAMPLE 5

44.028 g of potassium dihydrogenphosphate and 1.999 g of dipotassium hydrogenphosphate were dissolved in about 4000 ml of distilled water. 100.0 g of sodium N-acetylneuraminate and 500 mg of benzalkonium chloride were added to the solution. Distilled water was added thereto to make the total amount of 5,000 ml. The solution was filtered through a membrane filter and the filtrate was poured into special vessels each in an amount of 10 ml. For each spraying, 0.05 ml of the product was used, which corresponded to 1 mg of the compound. pH of the product was 5.0 to 6.0 (0.067 M phosphate buffer solution).

EXAMPLE 6

2.787 g of acetic acid and 37.208 g of sodium acetate were dissolved in about 4,000 ml of distilled water. 50.0 g of sodium N-acetylneuraminate and 15.0 g of chlorobutanol were added to the solution. Distilled water was added thereto to make the total amount of 5,000 ml. The solution was filtered through a membrane filter and the filtrate was poured into special vessels each in an amount of 10 ml.. For each spraying 0.05 ml of the product (0.5 mg of the compound) was used. pH of the product was 5.0 to 6.0 (0.1 M acetate buffer solution).

EXAMPLE 7

71.765 g of sodium dihydrogenphosphate and 5.67 g of disodium dihydrogenphosphate were dissolved in about 4,000 ml of distilled water. 1.30 g of methyl p-hydroxybenzoate and 0.70 g of propyl p-hydroxybenzoate were dissolved therein. 400.0 g of sodium N-acetylneuraminate was added to the solution. Distilled water was added thereto to make the total amount of 5,000 ml. The solution was filtered through a membrane filter and the filtrate was poured into special vessels each in an amount of 10 ml. They were sterilized with high-pressure steam in an ordinary manner. For each spraying, 0.05 ml of the product (4 mg of the compound) was used. pH of the product was 6.0 to 7.0 (0.1 M phosphate buffer solution).

EXAMPLE 8

Preparation of nasal discs:
Round filter papers having a diameter of 3 mm were impregnated with sodium N-acetylneuraminate and then dried. Each disc contained 0.1 to 50 mg of the compound of the present invention. The disc was applied to the mucous membrane of the inferior turbinate.

EXAMPLE 9

Preparation of nasal discs:
Round filter papers having a diameter of 3 mm were impregnated with lithium N-acetylneuraminate and then dried. Each disc contained 0.1 to 50 mg of the compound of the present invention. The disc was applied to the mucous membrane of the inferior turbinate.

EXAMPLE 10

44.028 g of potassium dihydrogenphosphate and 1.999 g of dipotassium hydrogenphosphate were dissolved in about 4,000 ml of distilled water. 100.0 g of lithium N-acetylneuraminate and 500 mg of benzalkonium chloride were added to the solution. Distilled water was added thereto to make the total amount of 5,000 ml. The solution was filtered through a membrane filter and the filtrate was poured into special vessels each in an amount of 10 ml. For each spraying, 0.05 ml of the product (1 mg of the compound) was used. pH of the product was 5.0 to 6.0 (0.067 M phosphate buffer solution).

EXAMPLE 11

2.787 g of acetic acid and 37.208 g of sodium acetate were dissolved in about 4,000 ml of distilled water. 50.0 g of lithium N-acetylneuraminate and 15 g of chlorobutanol were added to the solution. Distilled water was added thereto to make the total amount of 5,000 ml. The solution was filtered through a membrane filter and the filtrate was poured into special vessels each in an amount of 10 ml. For each spraying, 0.05 ml of the product (0.5 m of the compound) was used. pH of the product was 5.0 to 6.0 (0.1 M acetate buffer solution).

EXAMPLE 12

71.765 g of sodium dihydrogenphosphate dihydrate and 5.67 g of disodium hydrogenphosphate were dissolved in about 4,000 ml of distilled water. 1.30 g of methyl p-hydroxybenzoate and 0.70 g of propyl p-hydroxybenzoate were dissolved in the solution. 400.0 g of lithium N-acetylneuraminate was added to the solution. Distilled water was added thereto to make the total amount of 5,000 ml. The solution was filtered through a membrane filter and the filtrate was poured into special vessels each in an amount of 10 ml. They were sterilized with high-pressure steam in an ordinary manner. For each spraying, 0.05 ml of the product (4 mg of the compound) was used. pH of the product was 6.0 to 7.0 (0.1 M phosphate buffer solution).

EXAMPLE 13

Preparation of nasal discs:
Round filter papers having a diameter of 3 mm were impregnated with potassium N-acetylneuraminate and then dried. Each disc contained 0.1 to 50 mg of the compound of the present invention. The disc was applied to the mucous membrane of the inferior turbinate.

EXAMPLE 14

44.028 g of potassium dihydrogenphosphate and 1.999 g of dipotassium hydrogenphosphate were dissolved in about 4,000 ml of distilled water. 100.0 g of potassium N-acetylneuraminate and 500 m9 of benzalkonium chloride were added to the solution. Distilled water was added thereto to make the total amount of 5,000 ml. The solution was filtered through a membrane filter and the filtrate was poured into special vessels each in an amount of 10 ml. For each spraying, 0.05 ml of the product (1 mg of the compound) was used. pH of the product was 5.0 to 6.0 (0.067 M phosphate buffer solution).

EXAMPLE 15

2.787 g of acetic acid and 37.208 g of sodium acetate were dissolved in about 4,000 ml of distilled water. 50.0 g of potassium N-acetylneuraminate and 15.0 g of chlorobutanol were added to the solution. Distilled water was added thereto to make the total amount 5,000 ml. The solution was filtered through a membrane filter and the filtrate was poured into special vessels each in an amount of 10 ml. For each spraying, 0.05 ml of the product (0.5 mg of the compound) was used. pH of the product was 5.0 to 6.0 (0.1 M acetate buffer solution).

EXAMPLE 16

71.765 g of sodium dihydrogenphosphate dihydrate and 5.67 g of disodium hydrogenphosphate were dissolved in about 4,000 ml of distilled water. 1.30 g of methyl p-hydroxybenzoate and 0.70 g of propyl p-hydroxybenzoate were dissolved therein. 400.0 g of potassium N-hydroxybenzoate was added to the solution. Distilled water was added thereto to make the total amount of 5,000 ml. The solution was filtered through a membrane filter and the filtrate was poured into special vessels each in an amount of 10 ml. They were sterilized with high-pressure steam in an ordinary manner. For each spraying, 0.05 ml of the product (4 mg of the compound) was used. pH of the product was 6.0 to 7.0 (0.1 M phosphate buffer solution).

EXAMPLE 17

Preparation of nasal discs:

Round filter papers having a diameter of 3 mm were impregnated with barium N-acetylneuraminate and then dried. Each disc contained 0.1 to 50 mg of the compound of the present invention. The disc was applied to the mucous membrane of the inferior turbinate.

EXAMPLE 18

44.028 g of potassium dihydrogenphosphate and 1.999 g of dipotassium hydrogenphosphate were dissolved in about 4,000 ml of distilled water. 100.0 g of barium N-acetylneuraminate and 500 mg of benzalkonium chloride were added to the solution. Distilled water was added thereto to make the total amount of 5,000 ml. The solution was filtered through a membrane filter and the filtrate was poured into special vessels each in an amount of 10 ml. For each spraying, 0.05 ml of the product (1 mg of the compound) was used. pH of the product was 5.0 to 6.0 (0.067 M phosphate buffer solution).

EXAMPLE 19

2.787 g of acetic acid and 37.208 g of sodium acetate were dissolved in about 4,000 ml of distilled water. 50.0 g of barium N-acetylneuraminate and 15.0 g of chlorobutanol were added to the solution. Distilled water was added thereto to make the total amount of 5,000 ml. The solution was filtered through a membrane filter and the filtrate was poured into special vessels each in an amount of 10 ml. For each spraying, 0.05 ml of the product (0.5 mg of the compound) was used. pH of the product was 5.0 to 6.0 (0.1 M acetate buffer solution).

EXAMPLE 20

71.765 g of sodium dihydrogenphosphate dihydrate and 5.67 g of disodium hydrogenphosphate were dissolved in about 4,000 ml of distilled water. 1.30 g of methyl p-hydroxybenzoate and 0.70 g of propyl p-hydroxybenzoate were dissolved in the solution. 400.0 g of barium N-acetylneuraminate was added thereto. Distilled water was added thereto to make the total amount of 5,000 ml. The solution was filtered through a membrane filter and the filtrate was poured into special vessels each in an amount of 10 ml. They were sterilized with high-pressure steam in an ordinary manner. For each spraying, 0.05 ml of the product (4 mg of the compound) was used. pH of the product was 6.0 to 7.0 (0.1 M phosphate buffer solution).

EXAMPLE 21

Preparation of nasal discs:

Round filter papers having a diameter of 3 mm were impregnated with magnesium N-acetylneuraminate and then dried. Each disc contained 0.1 to 50 mg of the compound of the present invention. The disc was applied to the mucous membrane of the inferior turbinate.

EXAMPLE 22

44.028 g of potassium dihydrogenphosphate and 1.999 g of dipotassium hydrogenphosphate were dissolved in about 4,000 ml of distilled water. 100.0 g of magnesium N-acetylneuraminate and 500 mg of benzalkonium chloride were added to the solution. Distilled water was added thereto to make the total amount of 5,000 ml. The solution was filtered through a membrane filter and the filtrate was poured into special vessels each in an amount of 10 ml. For each spraying, 0.05 ml of the product (1 mg of the compound) was used. pH of the product was 5.0 to 6.0 (0.067 M phosphate buffer solution).

EXAMPLE 23

2.787 g of acetic acid and 37.208 g of sodium acetate were dissolved in about 4,000 ml of distilled water. 50.0 g of magnesium N-acetylneuraminate and 15.0 g of chlorobutanol were added to the solution. Distilled water was added thereto to make the total amount of 5,000 ml. The solution was filtered through a membrane filter and the filtrate was poured into special vessels each in an amount of 10 ml. For each spraying, 0.05 ml of the product (0.5 mg of the compound) was used. pH of the product was 5.0 to 6.0 (0.1 M acetate buffer solution).

EXAMPLE 24

71.765 g of sodium dihydrogenphosphate dihydrate and 5.67 g of disodium hydrogenphosphate were dissolved in about 4,000 ml of distilled water. 1.30 g of methyl p-hydroxybenzoate and 0.70 g of propyl p-hydroxybenzoate were dissolved therein. 400.0 g of magnesium N-acetylneuraminate was added to the solution. Distilled water was added thereto to make the total amount of 5,000 ml. The solution was filtered through a membrane filter and the filtrate was poured into special vessels each in an amount of 10 ml. They were sterilized with high-pressure steam in an ordinary manner. For each spraying, 0.05 ml of the product (4 mg of the compound) was used. pH of the product was 6.0 to 7.0 (0.1 M phosphate buffer solution).

In the above examples, the activities of the N-acetylneuraminate of lithium, potassium, sodium, balium and magnesium were described. However, it is expected that the calcium, ammonium and organic ammonium salts also provide substantially the same activities as the above salts.

What is claimed is:

1. A method of treating an animal suffering from nasal obstruction symptoms, which comprises applying to the nasal mucous membranes of the sufferer an effective amount of a compound of the formula:

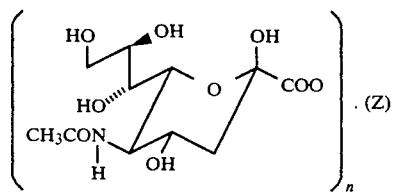
wherein Z represents lithium, potassium, sodium, ammonium or an organic ammonium when n is 1, and Z represents calcium, barium or magnesium when n is 2.
2. The method according to claim 1, wherein said compound is applied in the form of a spray, nasal drops or a disc.
* * * * *